US00PP33828P2

(12) United States Plant Patent
Beekenkamp

(10) Patent No.: US PP33,828 P2
(45) Date of Patent: Jan. 4, 2022

(54) ***BEGONIA* PLANT NAMED 'BKPBEBO'**

(50) Latin Name: ***Begonia* x *hiemalis***
Varietal Denomination: BKPBEBO

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 17/182,974

(22) Filed: Feb. 23, 2021

(51) Int. Cl.
*A01H 5/02* (2018.01)
*A01H 6/18* (2018.01)

(52) U.S. Cl.
USPC ..... Plt./348
CPC ..... *A01H 6/185* (2018.05)

(58) Field of Classification Search
USPC ..... Plt./348
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Begonia* plant named 'BKPBEBO', characterized by its compact, broadly upright and mounded plant habit; sturdy plants with freely basal branching habit; dark green-colored leaves; uniform and freely flowering habit; and double-type flowers that are bright red in color.

2 Drawing Sheets

Figure 1:
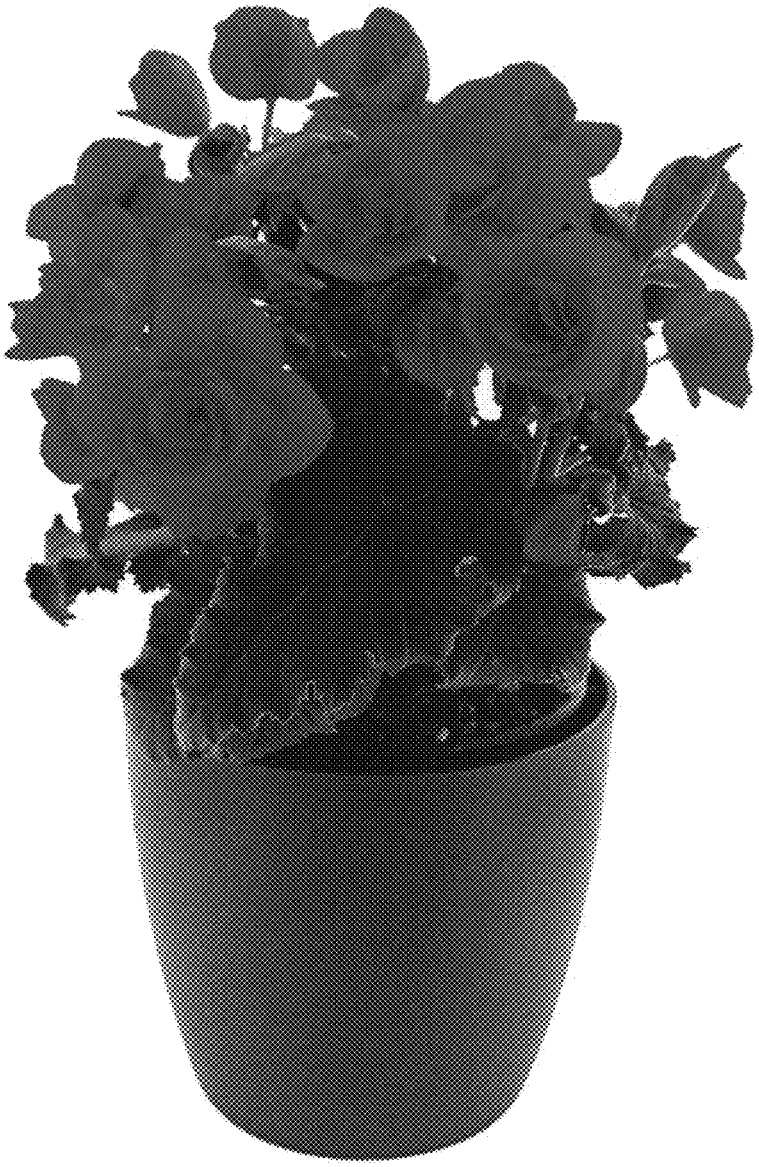

Botanical designation: *Begonia* x *hiemalis*.
Cultivar denomination: 'BKPBEBO'.

STATEMENT REGARDING PRIOR DISCLOSURES BY THE INVENTOR/APPLICANT & ASSIGNEE

An European Community Plant Breeder's Rights application for the instant plant was filed by the Assignee, Beekenkamp Plants B.V. of Maasdijk, The Netherlands on Sep. 24, 2020, application number 2020/2333. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as Elatior *Begonia* and hereinafter referred to by the name 'BKPBEBO'.

The new *Begonia* plant is a product of a planned breeding program conducted by the Inventor in Maasdijk, The Netherlands. The objective of the breeding program was to develop new compact, freely branching and freely flowering *Begonia* plants with attractive flowers and good garden performance.

The new *Begonia* plant originated from a cross-pollination made by the Inventor in June, 2010 of a proprietary selection of *Begonia* x *tuberhybrida* identified as code number 09-0008-03, not patented, as the female, or seed, parent with an unnamed proprietary selection of *Begonia socotmana*, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in December, 2010.

Asexual reproduction of the new *Begonia* plant by vegetative tip cuttings in a controlled greenhouse environment in Maasdijk, The Netherlands since February, 2011 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEBO'. These characteristics in combination distinguish 'BKPBEBO' as a new and distinct *Begonia* plant:

1. Compact, broadly upright and mounded plant habit.
2. Sturdy plants with freely basal branching habit.
3. Dark green-colored leaves.
4. Uniform and freely flowering habit.
5. Double-type flowers that are bright red in color.

Plants of the new *Begonia* can be compared to plants of the female parent selection. Plants of the new *Begonia* differ primarily from plants of the female parent selection in the following characteristics:

1. Plants of the new *Begonia* have smaller flowers than plants of the female parent selection.
2. Plants of the new *Begonia* have bright red-colored flowers whereas plants of the female parent selection have deep red-colored flowers.

Plants of the new *Begonia* can be compared to plants of the male parent selection. Plants of the new *Begonia* differ primarily from plants of the female parent selection in the following characteristics:

1. Plants of the new *Begonia* have larger flowers than plants of the male parent selection.
2. Plants of the new *Begonia* have bright red-colored flowers whereas plants of the male parent selection have pink-colored flowers.

Plants of the new *Begonia* can be compared to plants of *Begonia* x *hiemalis* 'BKPBECRM', disclosed in U.S. Plant Pat. No. 28,818. Plants of the new *Begonia* differ primarily from plants of 'BKPBECRM' in the following characteristics:

1. Plants of the new *Begonia* are more compact than plants of 'BKPBECRM'.
2. Plants of the new *Begonia* have smaller flowers than plants of 'BKPBECRM'.

Plants of the new *Begonia* can also be compared to plants of *Begonia* x *hiemalis* 'Baladin', not patented. Plants of the new *Begonia* differ primarily from plants of 'Baladin' in the following characteristics:

1. Plants of the new *Begonia* have smaller flowers than plants of 'Baladin'.
2. Plants of the new *Begonia* have bright red-colored flowers whereas plants of 'Baladin' have deep red-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical flowering plant of 'BKPBEBO' grown in a container.

Figure 2:
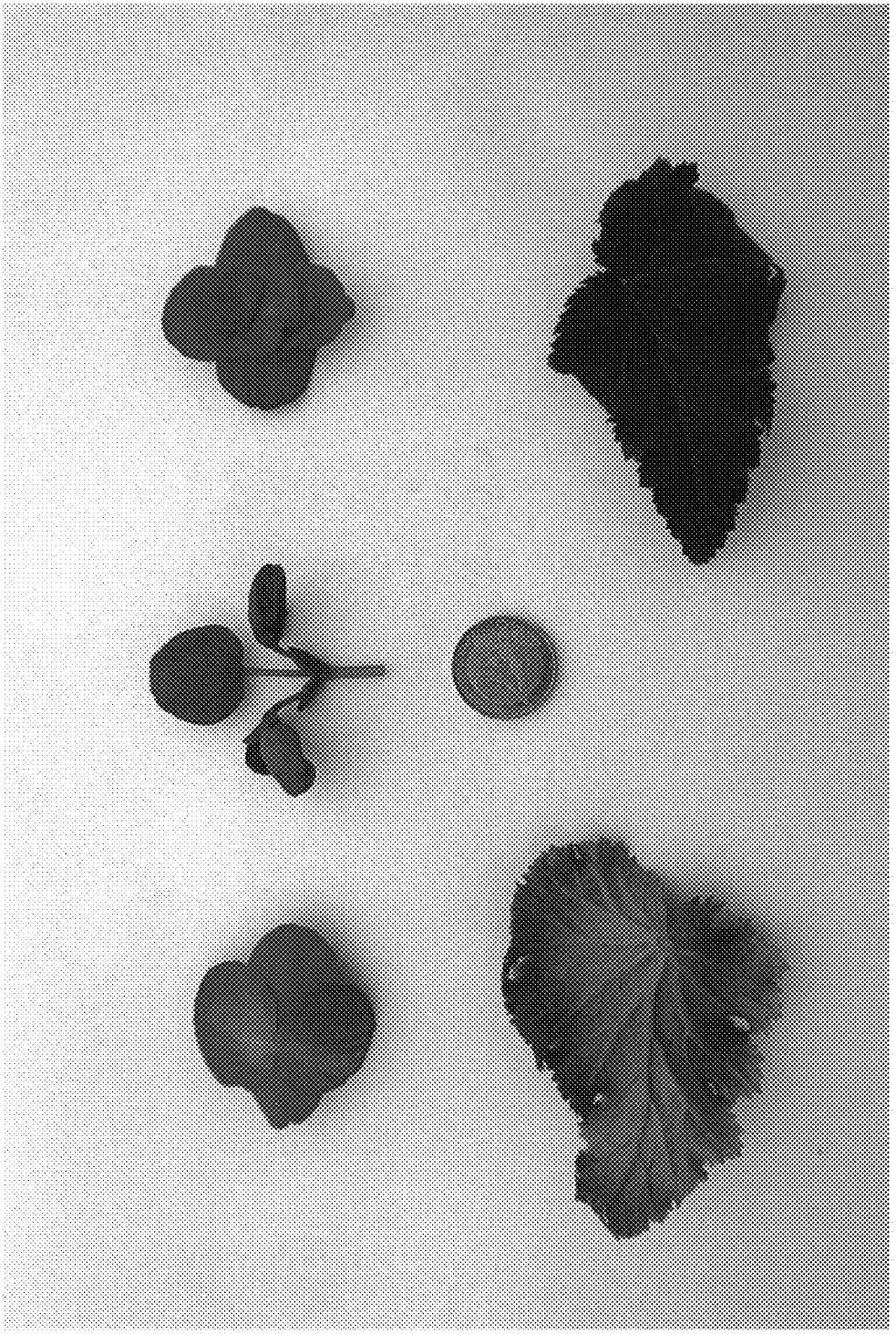

The photograph on the second sheet (FIG. 2) are close-up views of a typical flower bud and the upper and lower surfaces of typical developed flowers and leaves of 'BKPBEBO'.

DETAILED BOTANICAL DESCRIPTION

Plants used for the aforementioned photographs and following observations and measurements were grown during the autumn in 10.5-cm containers in a glass-covered greenhouse in Maasdijk, The Netherlands. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBEBO'.

Parentage:

*Female, or seed, parent*.—Proprietary selection of *Begonia* x *tuberhybrida* identified as code number 09-0008-03, not patented.

*Male, or pollen, parent*.—Unnamed proprietary selection of *Begonia socotmana*, not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; dense.

Plant description:

*Plant and growth habit*.—Compact, broadly upright and mounded plant habit; overall plant shape, broadly obovate to roughly globular; moderately vigorous growth habit and moderate growth rate.

*Plant height, soil level to top of foliar plane*.—About 13.6 cm.

*Plant height, soil level to top of floral plane*.—About 16.2 cm.

*Plant width*.—About 20.1 cm.

*Lateral branch description*.—Branching habit: Freely branching habit with about five basal branches per plant; pinching is not required. Length: About 6.6 cm. Diameter: About 6 mm to 7 mm. Internode length: About 2.1 cm. Strength: Moderately strong. Aspect: Erect to about 40° from vertical. Texture and luster: Sparsely pubescent; moderately glossy. Color, developing: Close to 144A; surfaces exposed to direct sunlight are tinged with close to 172B. Color, fully developed: Close to 146A tinged with close to 164A; at the nodes, close to 144A slightly tinged with close to 176D.

*Leaf description*.—Arrangement: Alternate, simple. Length: About 9.3 cm. Width: About 7.1 cm. Shape: Broadly ovate. Apex: Acute to bluntly acute. Base: Oblique, lobes occasionally imbricate. Margin: Serrate; moderately to strongly undulate and slightly crispate. Texture and luster, upper surface: Smooth, glabrous; slightly velvety; moderately glossy. Texture and luster, lower surface: Mostly smooth and glabrous with sparse pubescence along the veins; velvety; slightly glossy. Venation pattern: Pinnate. Color: Developing leaves, upper surface: Close to 141A; margins, strongly tinged with close to 178A. Developing leaves, lower surface: Close to 146B to 146C slightly tinged with close to 177C; margins, strongly tinged with close to 178A. Fully expanded leaves, upper surface: Darker than between 139A and N189A; venation, close to 137B. Fully expanded leaves, lower surface: Close to 148B slightly tinged with close to 178A; venation, close to 146B. Petioles: Length: About 4.1 cm. Diameter: About 3 mm. Strength: Flexible. Texture and luster, upper and lower surfaces: Sparsely to moderately pubescent; moderately glossy. Color, upper surface: Close to between 152A and 199A; at distal end, strongly tinged with close to 183B. Color, lower surface:

Close to 199A; at proximal and distal ends, strongly tinged with close to 183B. Stipules: Quantity per leaf: Two at the base of the leaf. Length: About 8 mm. Width: About 8 mm. Shape: Broadly ovate. Apex: Obtuse to bluntly acute. Base: Broadly cuneate. Margins: Finely ciliate.

Flower description:

*Flowering habit*.—Rotate double-type sterile male flowers arranged in axillary compound cymes; freely flowering habit with about five flowers per cyme and about 200 flowers developing per plant during the flowering season; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about 45 days after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 9.7 cm.

*Inflorescence diameter*.—About 7.1 cm.

*Flower buds*.—Length: About 1.9 cm. Diameter, flattened: About 0.6 cm to 2 cm. Shape: Obovate; flattened. Texture and luster: Smooth, glabrous; velvety; matte, towards the base, slightly glossy. Color: Close to 46A; towards the margins, close to 53A.

*Flowers*.—Diameter: About 5.1 cm. Depth: About 1.8 cm. Tepals: Quantity and arrangement: Two per flower, opposite. Length: About 2.6 cm. Width: About 2.7 cm. Shape: Broadly ovate to close to orbicular. Apex: Rounded. Base: Broadly cuneate to shallowly truncate. Margin: Entire; not undulate. Texture and luster, upper surface: Smooth, glabrous, velvety; matte. Texture and luster, lower surface: Smooth, glabrous, slightly velvety; slightly glossy. Color: When opening, upper surface: Close to 45B; towards the margins, close to N45B. When opening, lower surface: Close to N34A and 42A. Fully opened, upper surface: Close to N45B; towards the base, close to 46C; venation, close to 182B; color does not fade with development. Fully opened, lower surface: Close to between 42A and 42B; venation, close to 180A; color does not fade with development. Tepaloids: Quantity and arrangement: About 38 arranged in about seven whorls interior to the tepals. Length: About 1.7 cm, varying between 0.4 cm and 2.5 cm. Width: About 1.6 cm, varying between 0.4 cm and 2.9 cm. Shape: Reniform to obovate. Apex: Obtuse to rounded. Base: Cuneate to broadly cuneate. Margin: Entire; not undulate. Texture and luster, upper surface: Smooth, glabrous, velvety; matte. Texture and luster, lower surface: Smooth, glabrous, moderately velvety; matte. Color: When opening, upper surface: Close to 45B; centers, close to 51B and 51C; main vein, close to 11D. When opening, lower surface: Close to 45B; centers, close to 51B. Fully opened, upper surface: Close to 45B; towards the base, close to 46C and irregularly flushed with close to 50C and 12B to 12C; venation, faint, close to 182B; color does not fade with development. Fully opened, lower surface: Close to 45B; towards the base, close to 46C and irregularly flushed with close to 50C and 4A; venation, close to 182A; color does not fade with development.

*Peduncles*.—Length: About 3.9 cm. Diameter: About 3 mm to 3.5 mm. Angle: About 60° from lateral branch axis. Strength: Moderately strong; flexible. Texture and luster: Sparsely pubescent; moderately glossy. Color: Close to 152A and 152B.

*Pedicels*.—Length: About 2.6 cm. Diameter: About 2 mm. Angle: About 30° from the peduncle axis. Strength: Moderately strong; flexible. Texture and luster: Moderately pubescent; moderately glossy. Color: Close to 174A and 185A.

*Flower bracts*.—Quantity and arrangement: Two per flower, opposite. Length: About 1 cm. Width: About 0.95 cm. Shape: Broadly ovate. Apex: Praemorse. Base: Broadly cuneate. Margin: Finely ciliate. Texture and luster, upper and lower surfaces: Smooth, glabrous; very slightly glossy. Color, upper and lower surfaces: Close to 178A to slightly darker than 178A; towards the base, close to 147A and 147B.

*Reproductive organs*.—None observed, all structures transformed into tepaloids.

*Seeds and fruits*.—Seed and fruit development have not been observed on plants of the new *Begonia* as flowers are sterile.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEBO' as illustrated and described.

* * * * *